United States Patent [19]

Chickering et al.

[11] Patent Number: 4,968,311
[45] Date of Patent: Nov. 6, 1990

[54] ATTACHED WRAPPER FLAPS FOR THE CONSIDERATE DISPOSAL OF INFANT DISPOSAL DIAPERS

[75] Inventors: Robert Chickering, Corona Del Mar, Calif.; William A. Barabino, North Reading, Mass.

[73] Assignee: Personal Hygiene Research Associates, North Reading, Mass.

[21] Appl. No.: 416,226

[22] Filed: Oct. 2, 1989

[51] Int. Cl.[5] ............................................. A61F 13/16
[52] U.S. Cl. ................................................. 604/385.1
[58] Field of Search ....................................... 604/385.1

[56] References Cited

U.S. PATENT DOCUMENTS

| | | | |
|---|---|---|---|
| 3,585,999 | 6/1971 | Wanberg | 604/385.1 |
| 3,731,689 | 5/1973 | Schaar | 604/385.1 |
| 3,920,019 | 11/1975 | Schaar | 604/385.1 |
| 4,430,087 | 2/1984 | Azpiri | 604/385.1 |
| 4,604,096 | 8/1986 | Dean et al. | 604/385.2 |

Primary Examiner—Randall L. Green
Assistant Examiner—Gary Jackson
Attorney, Agent, or Firm—Richard C. Litman

[57] ABSTRACT

A disposable infant's diaper includes a wrapper comprising a unitary sheet having a base panel affixed to the diaper back section to form a pocket within which the balance of the wrapper sheet is contained. When the diaper is soiled and the user wishes to dispose of it, pulling an end panel of the sheet from the pocket unfolds the sheet to present lateral flaps bounding a center panel, while the sheet remains affixed to the diaper. The diaper is over-folded onto the sheet center panel, after which the lateral flaps are sequentially over-folded atop the diaper and respectively sealingly attached in place. The complete encapsulation of the diaper is achieved following the over-folding of the sheet end panel atop the previously manipulated lateral flaps. Alternative folded configurations of the wrapper sheet are contemplated.

8 Claims, 4 Drawing Sheets

ATTACHED WRAPPER FLAPS FOR THE CONSIDERATE DISPOSAL OF INFANT DISPOSAL DIAPERS

BACKGROUND OF THE INVENTION

The present invention relates generally to disposable infant diapers and more particularly, to an infant diaper provided with improved means, in the form of an attached wrapper, allowing for the complete encapsulation of the diaper when soiled, thereby permitting its considerate disposal. Considerate disposal refers to the reduction of the unpleasantness associated with the disposal of a soiled infant diaper and addresses means enhancing the hygienic manipulation and subsequent disposal thereof.

DESCRIPTION OF THE PRIOR ART

An example of a known approach to the encapsulation of a used diaper prior to disposal will be found in U.S. Pat. No. 4,604,096 which is directed to an integral envelope for the sanitary disposal of adult incontinent undergarments (diapers). U.S. Pat. No. 4,430,087 discloses an example of a diaper provided with a storage device but this is in the form of a bag and which is preliminarily retained between layers of the diaper. Neither of these examples are seen to even remotely hint at the unique construction as presented by the present invention. Though the disposal of adult incontinent undergarments has been described heretofore, the disposal of infant diapers has been poorly addressed.

For the most part, such a useful device has not yet been introduced, because it is inappropriate to have a removable bag attached to an infant's diaper. It is possible in such a circumstance that the infant could remove the bag inadvertently and an infant having access to a plastic bag is not considered to be in the best interest of safety.

SUMMARY OF THE INVENTION

As a result of the shortcomings of existing art, the present invention addresses the need for convenient means for the simple disposal of soiled infant diapers in a hygienic manner. This is achieved by the incorporation of an impervious cover material in the form of a packaged wrapper, into the diaper and that may be readily opened up and subsequently enveloped about a folded diaper to completely encapsulate it for considerate disposal. The wrapper is constructed in a pre-use packaged configuration such that an infant can not inadvertently remove it prior to an attendant's disposal of the diaper. Even if an infant were able to open the wrapper package assembly, in view of its basic planar, sheet-like construction, no bag will be presented as the attached wrapper sheet is opened.

Accordingly, it is an object of the present invention to provide an improved disposable diaper including an attached wrapper assembly comprising a unitary sheet of material initially folded into a compact package and which is actuated by withdrawal of a pull tab.

Another object of the present invention is to provide an improved disposable diaper including an attached folded wrapper comprising a sheet having a plurality of integral panels adapted to be over-folded the four sides of a folded soiled diaper to fully encapsulate it.

Still another object of the present invention is to provide an improved disposable diaper containing a folded single sheet wrapper forming its own pocket and attached to the back side of a diaper.

A further object of the present invention is to provide a cover material for the considerate disposal of infants' diapers that is manufactured separately of the diaper and may be sealingly affixed to disposable diapers of various constructions.

Another object of the present invention is to provide an encapsulation apparatus for the considerate disposal of an infant's diaper that can be manufactured inexpensively and readily attached to any of various disposable diapers without a noticeable increase in bulk or expense.

With these and other objects in view which will more readily appear as the nature of the invention is better understood, the invention resides in the novel construction, combination and arrangement of parts hereinafter more fully described and illustrated with reference being made to the accompanying drawings.

BRIEF DESCRIPTION OF THE DRAWINGS

Similar reference characters designate corresponding parts throughout the various figures of the drawings.

DESCRIPTION OF THE PREFERRED EMBODIMENT

Figure 1:
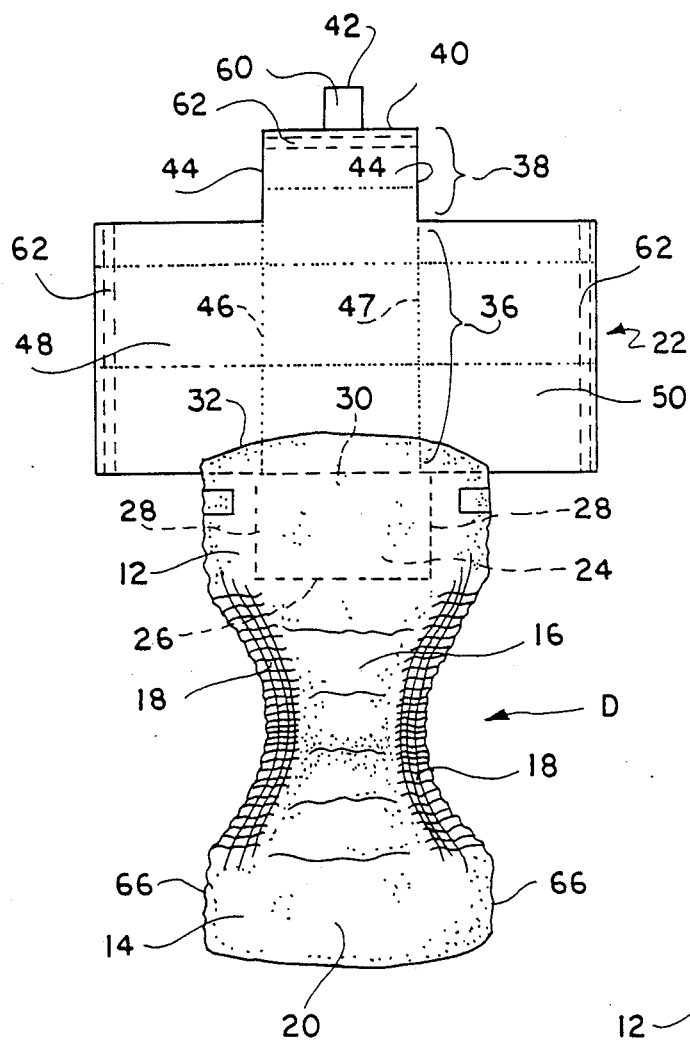
FIG. 1 is a top plan view of the inner side of a diaper illustrating the disposal wrapper assembly of the present invention as it appears when opened for encapsulation of a soiled diaper.
Figure 2:
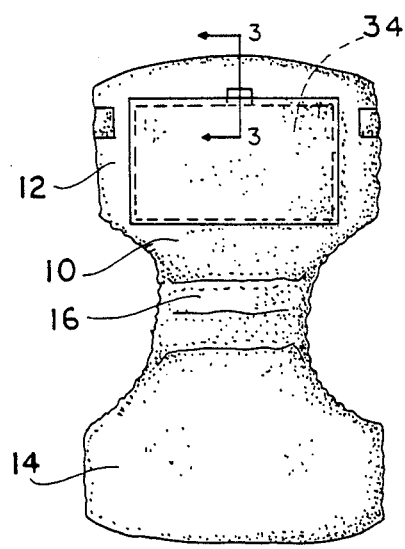
FIG. 2 is a top plan view of the back side of the diaper of FIG. 1, with the disposal wrapper assembly folded and in its self-storage condition.

Referring now to the drawings, particularly FIGS. 1 and 2, the present invention will be understood to relate to a disposal wrapper assembly W as utilized for encapsulating a diaper D, when soiled. The specific construction of the diaper D may vary in accordance with this invention since a feature thereof is that the instant wrapper W is adaptable to the outer face 10 of variously configured disposable infant diapers. Such a diaper may include a rear or back section 12 joined to a front section 14 by an intermediate crotch section 16, the latter of which is preferably of lesser width and includes shirred or elasticized hems 18,18.

As will be seen in FIG. 1, which illustrates the inner face 20 of the diaper D, the wrapper W when withdrawn from its stored, prior-to-use position of FIG. 2, comprises a single, unitary sheet 22 of material which may be of any suitable well known liquid impervious composition. Preferably, this sheet material is thermoplastic, in order to lend itself to heat sealing as will be described hereinafter. The sheet 22 includes a base panel 24 with its lower edge 26 and two adjacent lateral edges 28,28 appropriately affixed, as by heat sealing, to the outer face 10 of the diaper back section 12 so that the imaginary top line 10 of the base panel 24 is adjacent to but spaced from, the diaper back section waist line 32. In this manner, it will be appreciated that the attached sheet base panel 24 provides a pocket 34 therebeneath, accessible &rom the direction of the diaper waist line 32.

The wrapper sheet 22 includes a center section or panel adjacent the base panel 24 and from which axially extends an end panel or flap 38, terminating in an outer edge 40 from which may extend a pull tab 42. The two lateral edges 44,44 of the end flap 38, if extended, will be seen to define imaginary fold lines 46,40 terminating at the base panel top line 30, at points which are slightly spaced inwardly from the base panel lateral edges 28,28 for reasons will become apparent hereinafter.

Laterally projecting from the respective sides 46 of the center panel 36 are first lateral flap 48 and second lateral flap 50, the lateral extent of each of which is preferably no less than that of the center panel 86. The axial extent of the center panel 36 is preferably at least one-third the over-all length of the associated diaper D. This will insure that a sufficient area of the sheet 22 will be available to fully encapsulate a soiled diaper when enveloped by the wrapper W.

Figure 3:
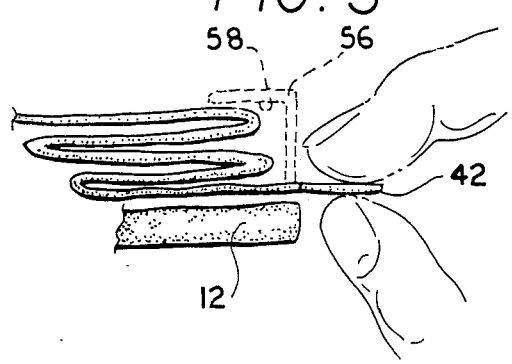
FIG. 3 is a cross-sectional view, taken along the line 8—8 of FIG. 2.
Figure 4:
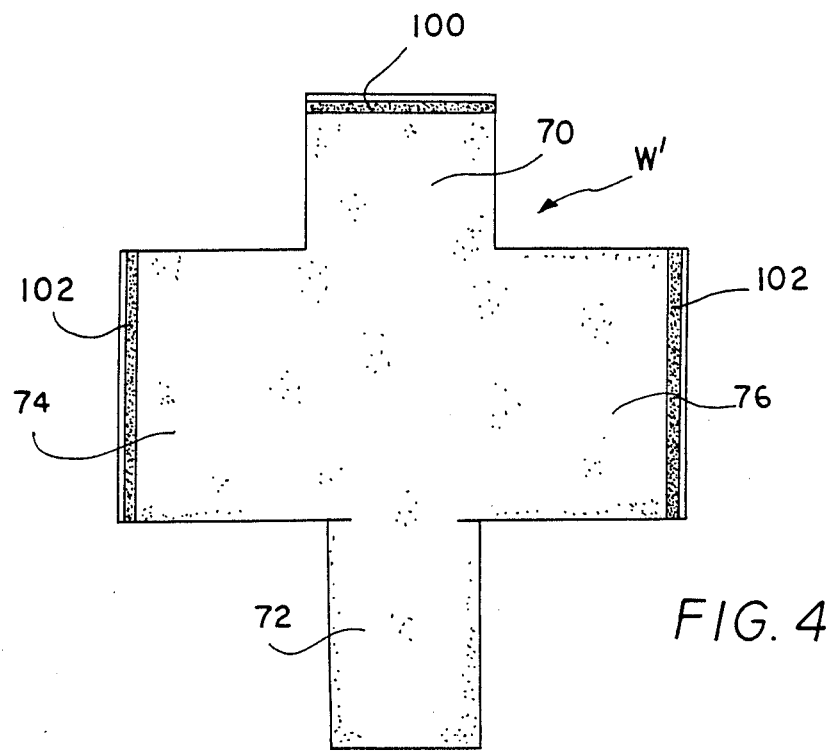
FIGS. 4—13 are plan views showing a typical manner of folding the plurality of wrapper sheet panels to provide the self-storage pocket as shown in FIG. 2.
Figures 5, 6:
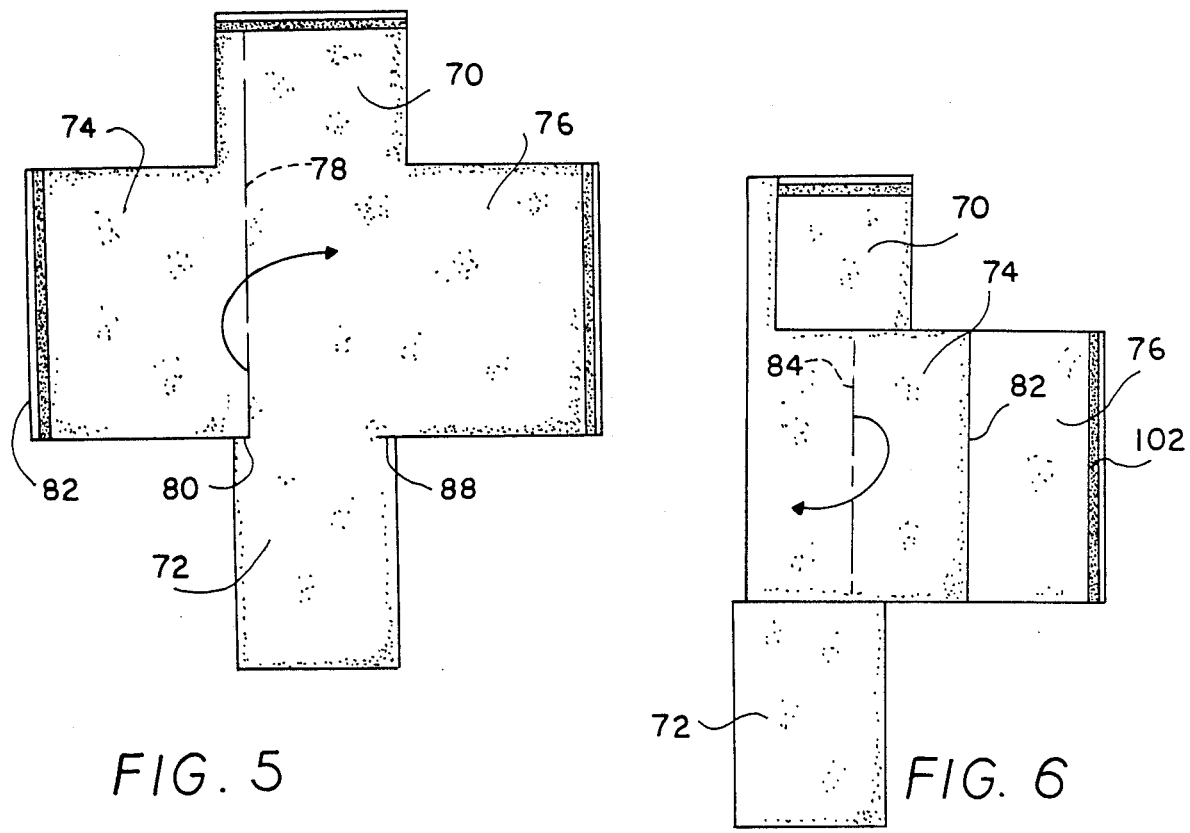

When a customer initially applies the diaper D about an infant, the wrapper sheet 22 is fully contained within the pocket 34 as formed by the wrapper base panel 24. To receive all of the wrapper sheet 22 below the base panel top edge 30, the sheet is folded in any suitable manner which will result in a relatively flat, stacked assembly of the plurality of sheet areas. This folding operation of course occurs during the manufacture of the wrapper assembly W prior to its attachment to the diaper back section 12 and consideration is given to a folding sequence which lends itself to a ready withdrawal of the sheet from within the pocket 34 and a convenient opening up of the folded sheet portions to arrive at the ready-to-use planar sheet 22 as pictured in FIG. 1 of the drawings A suggested folding of the sheet will be seen from FIGS. 1 and 8. Initially the laterals flaps 48,50 are over-folded the center panel 36, along the imaginary fold lines 46,47 and thereafter the partially folded wrapper is zig-zag or accordion folded to axially collapse it into the nested position beneath the base panel 24. The packaged wrapper W will then appear as in FIGS. 2 and 3 wherein the pull tab 42 may either overlie the diaper back section 12 or be folded back over the top edge of the base panel 24, as reflected by the broken lines 66 in FIG. 3. At least in the latter instance, pressure sensitive adhesive 58 is provided on the top or inner surface 60 of the tab 42 to retain it against the base panel 24. Additionally, pressure sensitive adhesive layers 62 are provided on the sheet top surface 60 of each lateral flap 48,50, adjacent its edge 64 as well as on the end flap 38 adjacent its outer edge 40.

With the foregoing wrapper structure in mind, the manner of utilizing it to envelope a soiled diaper D may now be described. the diaper is placed upon a supporting surface (not shown) with its inner face 20 upper most and then the user grasps the wrapper tab 42 to withdraw the sheet 22 from within the pocket 34, thereby fully axially extending the wrapper. Then, the lateral flaps 48,50 are opened to the flat condition as shown in FIG. 1. In actual practice, the side edges 66 of a soiled diaper's front and back sections 14,12 will be somewhat curled inwardly, thereby reducing the lateral extent from that as shown in FIG. 1. In any case the user will encourage such inward folding or curling to insure reduction of the width of the diaper to that more closely approximating the width of the crotch section 16. The diaper front section is then folded upwardly about the center of the crotch section 16 and thence folded upwardly again thereby reducing its axial extent by one-fourth, with the majority of the folded diaper overlying the wrapper base panel 24.

The thusly folded diaper D is then over-folded onto the top surface 60 of the wrapper center panel 36 whereupon it will be sandwiched intermediate the center panel and base panel 24. Next, one of the lateral flaps 48 or 50 are over-folded the diaper, along its imaginary fold line 46 or 47. The other lateral flap is next over-folded the previously folded lateral flap. Just prior to each lateral flap being over-folded, its pressure sensitive adhesive layer 62 is exposed by the removal of a protective strip (not shown), so that the over-folded flap may be secured to the base panel or previously folded lateral flap. The complete envelopment of the soiled diaper is accomplished by the subsequent over-folding of the end flap 38 after similarly exposing its pressure sensitive layer 62.

From the foregoing it will be appreciated that the folded soiled diaper D will be fully enveloped from all four sides, by the plurality of panels or flaps of the unitary wrapper W which at all times remains affixed to the outer face 10 of the diaper such that an enhanced encapsulation of the diaper is achieved.

Figure 7:
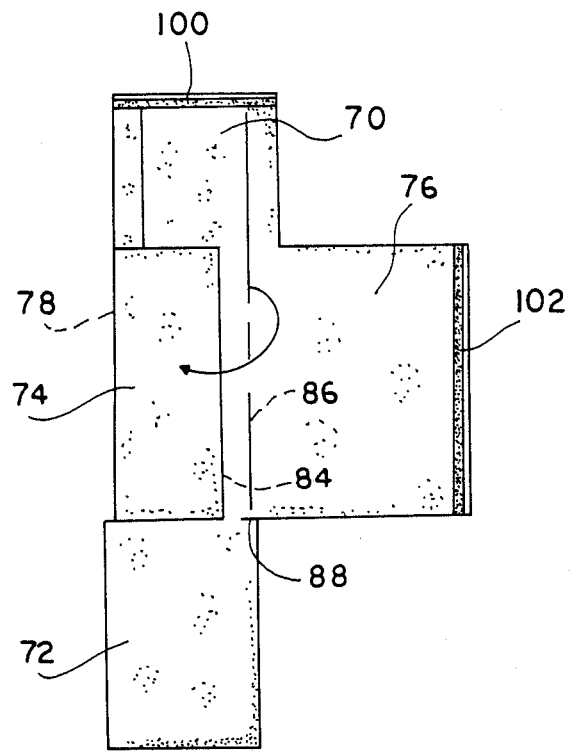
Figure 8:
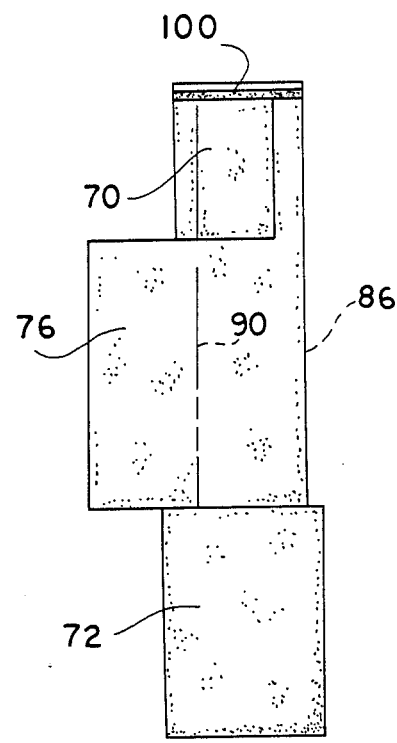

FIGS. 4-13 most clearly depict an alternative wrapper assembly W' wherein the end panel or flap 70 will be seen to define a width greater than that of the base panel 72 and which is counter to the construction of the first described embodiment. With this latter configuration, each lateral flap defines a width substantially greater than that of the base panel. Since it is this base panel which will form the pocket to receive the remainder of the wrapper W', obviously the lateral flaps 74,76, when over-folded, as well as the end panel 70, must define a width less than that of the base panel 72. Accordingly, the left lateral flap 74 is over-folded along the imaginary line 78 which will be seen from FIGS. 4 and 5 to intersect the slit 80 formed along the top line of the base panel 72. Thereafter, the outer edge 82 of the flap 74 is over-folded, along the medial axis 84 of the flap 74 from the position of FIG. 6 to that of FIG. 7. The same procedure is followed with respect to the right lateral flap 76. That is it is over-folded along the line 86 which intersects the slit 68, and then over-folded upon itself, along the medial axis 90, as shown in FIGS. 7 and 8.

Figure 9:
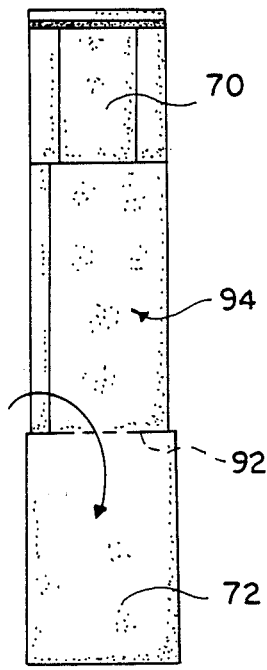

The wrapper W' will then appear as in FIG. 9 wherein it will be seen that the width of all of the sheet beyond the base panel top line defines a dimension less than that of the base panel 72. Thereafter, the axial extent of the wrapper W' is progressively reduced by initially over-folding the combination of the lateral flaps and center panel 64 and end panel 70 downwardly to overlie the base panel 72. The package is accordingly altered from the position of FIG. 9 to that of FIG. 10

Figure 10:
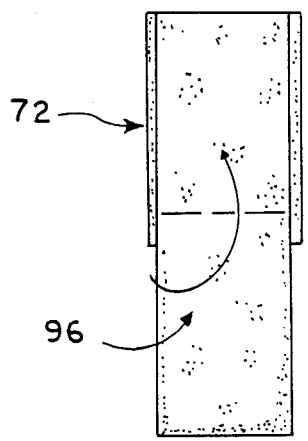
Figure 11:
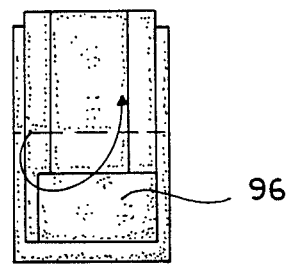
Figure 12:
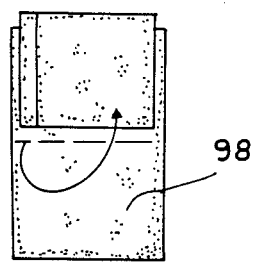
Figure 13:
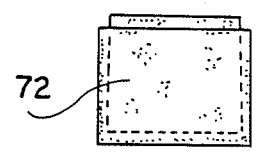

The next step involves over-folding the end panel and portion of the center panel, now shown as 96 in FIG. 10, to overlie the remaining portion of the center section and the base panel, to yield the arrangement as viewed in FIG. 11. The resultant segment 96 is thence over-folded onto the upper area of the package, as shown in FIG. 12, after which, the lower half 98 of the base panel 72 is over-folded the balance of the assembly to provide the completed wrapper assembly W', ready to affix to a diaper. The end panel 72 may be provided with either of the pull tabs 42,56 of the first described embodiment while similar pressure sensitive adhesive layers 100,102 are provided to accomplish the fixation of the end panel and lateral flaps during envelopment of a soiled diaper by means of the wrapper W'. The base panel 72 will be understood to be affixed to the back section 12 of a diaper, as in the earlier described wrapper W.

We claim:

1. A wrapper for enveloping a soiled disposable diaper having a back section provided with an outer face, comprising;
   a sheet including a center panel juxtaposed opposite lateral flaps terminating in outer edges defining a width therebetween greater than the width of said diaper,
   an end panel on said sheet projecting beyond said center panel and axially aligned with said diaper,
   said center panel affixed to said diaper outer face, and
   cover means on said sheet permitting storage of said sheet center panel, end panel and lateral flaps in a sandwiched disposition contiguous with said diaper outer face.

2. A wrapper for enveloping a soiled disposable diaper according to claim 1 wherein,
   said wrapper sheet comprises a unitary member.

3. A wrapper for enveloping a soiled disposable diaper according to claim 1 wherein,
   said wrapper sheet comprises a liquid impervious material.

4. A wrapper for enveloping a soiled disposable diaper according to claim 1 wherein,
   said cover means comprises a base panel integral with said sheet.

5. A wrapper for enveloping a soiled disposable diaper according to claim 1 including,
   a pull tab on said end panel.

6. A wrapper for enveloping a soiled disposable diaper according to claim 1, wherein,
   said wrapper sheet center panel, lateral flaps and end panel are initially over-folded upon one another to define a planar area less than that of said cover means.

7. A wrapper for enveloping a soiled disposable diaper according to claim 1 wherein,
   said center panel defines an axial extent no less than one-third the axial extent of said diaper, whereby
   upon the over-folding of said diaper upon itself twice, the folded diaper may be fully contained in an overlying manner upon said center panel.

8. A wrapper for enveloping a soiled disposable diaper according to claim 4 wherein,
   said base panel comprises a substantially rectangular member having a bottom edge and adjacent lateral edges, and
   said base panel edges heat sealed to said diaper outer face.

* * * * *